US00PP09231P

United States Patent [19]

Trees

[11] Patent Number: Plant 9,231

[45] Date of Patent: Aug. 1, 1995

[54] GERANIUM PLANT NAMED 'PINK PEARL'

[75] Inventor: Scott C. Trees, Arroyo Grande, Calif.

[73] Assignee: Geo. J. Ball, Inc., West Chicago, Ill.

[21] Appl. No.: 341,915

[22] Filed: Nov. 15, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 7,087 12/1968 Hofmann ..... Plt./87.12
P.P. 8,005 10/1992 Hofmann ..... Plt./87.12
P.P. 8,522 12/1993 Trees ..... Plt./87.12

*Primary Examiner*—James R. Feyrer
*Attorney, Agent, or Firm*—Burns, Doane, Swecker & Mathis

[57] ABSTRACT

A new and distinct *Pelargonium*×*hortorum* cultivar named Pink Pearl is provided. This new Zonal Geranium was the result of a controlled breeding program wherein the Light Pink cultivar (U.S. Plant Pat. No. 8,552) was pollinated by the Laura cultivar (U.S. Plant Pat. No. 7,087). The new cultivar forms attractive perfectly formed semi-double light lavender pink florets with white eyes. The medium green foliage is well retained even during shipment. The growth habit is medium self-branching and does not require the use of a growth regulator.

1 Drawing Sheet

SUMMARY OF THE INVENTION

The present invention comprises a new and distinct Geranium cultivar, botanically known as *Pelargonium*-×*hortorum* Bailey, and is hereinafter referred to by the cultivar name Pink Pearl.

The new cultivar is the product of a planned breeding program which had as its objective the creation of a new Geranium cultivar that exhibits uniform flowers, medium green foliage, a medium self-branching growth habit that requires no growth regulator, a propensity for rapid rooting, and a stable foliage coloration during shipment.

The breeding program that resulted in the production of the new cultivar of the present invention was carried out during 1990 at Arroyo Grande, Calif., U.S.A. The female parent (i.e., seed parent) was the Light Pink cultivar (U.S. Plant Pat. No. 8,552) which exhibits semi-double light pink florets with medium green foliage. The male parent (i.e., pollen parent) was the Laura cultivar (U.S. Plant Pat. No. 7,087) which exhibits semi-double lavender florets and medium green foliage. The parentage of Pink Pearl can be summarized as follows:

Light Pink×Laura.

Pink Pearl was discovered and selected during 1991 as a distinctive flowering plant from among the progeny of the stated cross at Arroyo Grande, Calif., U.S.A. This plant was initially designated BFP-680.

It was found that the new cultivar of the present invention:

(a) exhibits attractive perfectly formed semi-double light lavender pink florets with white eyes,
(b) forms medium green foliage with zonation, and
(c) exhibits a medium self-branching growth habit.

When a plant material of the Pink Pearl cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of Pink Pearl cultivar was accomplished when vegetative cuttings were taken from the initial selection in a controlled environment at Arroyo Grande, Calif., U.S.A. by a technician working under the direction and supervision of the originator of the new cultivar. Horticultural examination of plants resulting from such asexual propagation during 1991 has demonstrated that the combination of unique characteristics as herein described for the Pink Pearl cultivar is firmly fixed and is retained through successive generations of such reproduction.

The new Pink Pearl cultivar has not been observed under all possible environmental conditions. Accordingly, the described phenotype may vary somewhat with variations in the environment, such as temperature, light intensity, and day length.

Of the many commercial cultivars known to the originator of the new cultivar of the present invention, the most similar is believed to be the Precious cultivar (U.S. Plant Pat. No. 8,005). When the new cultivar of the present invention is compared to the Precious cultivar, Pink Pearl is found to exhibit fewer umbels per plant (e.g., approximately 8 to 9 vs. approximately 9 to 11). However, each umbel of the new Pink Pearl cultivar commonly possesses more florets which are slightly larger than those of the Precious cultivar, thus producing larger umbels (e.g., approximately 9 to 10 cm.×approximately 6 to 7 cm. vs. approximately 8 to 9 cm.×approximately 5 to 6 cm.). The Pink Pearl cultivar also exhibits shorter peduncles and longer pedicels as specified in greater detail hereafter.

The new cultivar of the present invention is being marketed by Geo. J. Ball, Inc. under the Designer trademark.

BRIEF DESCRIPTION OF THE PHOTOGRAPH

The accompanying photograph shows a typical plant of the new Pink Pearl cultivar with colors being as nearly true as it is reasonably possible to make the same in a color illustration of this character. Typical flowers and foliage are depicted. The plant was grown in a greenhouse at West Chicago, Ill., U.S.A.

DETAILED DESCRIPTION

The following observations, measurements and comparisons describe plants grown in Ball FloraPlant's greenhouses located at West Chicago, Ill., U.S.A., under greenhouse conditions which approximate those generally used in commercial practice. In the following description, color references are made to the R.H.S. Colour Chart of The Royal Horticultural Society, London, England. The color values were determined between 9:00 and 10:00 a.m. on Jul. 21, 1994, under natural light conditions of 2,000 footcandles.

Classification:

*Botanical:*—*Pelargonium* × *hortorum* Bailey, cv. Pink Pearl.

*Commercial:*—Zonal Geranium.

INFLORESCENCE

A. Umbel:

*Average diameter.*—Approximately 9 to 10 cm. This can be compared to approximately 8 to 9 cm. for the Precious cultivar.

*Average depth.*—Approximately 6 to 7 cm. This can be compared to approximately 5 to 6 cm. for the Precious cultivar.

*Peduncle length.*—Approximately 14.5 to 15.5 cm. This can be compared to approximately 16 to 17 cm. for the Precious cultivar.

*Pedicel length.*—Approximately 2.5 to 3.0 cm. This can be compared to approximately 1.5 to 2.0 cm. for the Precious cultivar.

*Number of umbels plant.*—When grown in a 10 cm. pot at 9 weeks after the sticking of a rooted cutting, there commonly are 8 to 9 umbels per plant. This compares to approximately 9 to 11 umbels per plant for the Precious cultivar. When plants are grown in the field for 16 weeks the new cultivar commonly possesses approximately 17 umbels per plant while the Precious cultivar commonly possesses approximately 21 umbels per plant.

*Number of florets umbel.*—When grown in a 10 cm. pot at 9 weeks after the sticking of a rooted cutting, there commonly are approximately 25 to 28 florets per umbel. This compares to approximately 24 to 27 florets per umbel for the Precious cultivar.

B. Corolla:

*Average diameter.*—Approximately 4.5 to 5.0 cm. compared to approximately 4.3 to 4.5 cm. for the Precious cultivar.

*Form.*—Both the Pink Pearl and the Precious cultivars are semi-double.

*Number of Petaloids.*—The Pink Pearl cultivar commonly possesses 1 to 2 petaloids per floret whereas the Precious cultivar only occasionally possesses 1 petaloid per floret.

*Color*—General tonality from a distance of three meters: Orchid with a white eye. Adaxial: Red-Purple Group 73B with white patches on the upper two petals that extend to the attachment points. This compares to Purple Group 75A with white patches on the upper two petals for the Precious cultivar. Abaxial: Red-Purple Group 73D. This compares to Red-Purple Group 73B for the Precious cultivar.

C. Bud:

*Shape.*—Oval pointed.

*Color.*—Adaxial: Red-Purple Group 74A for Pink Pearl cultivar and Purple Group 75A for the Precious cultivar. Abaxial: Red-Purple Group 73D for Pink Pearl cultivar and Red-Purple Group 73B for the Precious cultivar.

D. Reproductive organs:

*Androecium.*—The anthers are commonly approximately 2 mm. in length. The pollen color is Orange-Red Group 30A for the Pink Pearl cultivar and Orange-Red Group 31A for the Precious cultivar. The filaments are approximately 5 to 7 mm. in length.

*Gynoecium.*—The pistil length commonly is approximately 9 mm. There is a single stigma which commonly has a length of approximately 4 mm. which commonly branches into 5 parts, and the style length commonly is approximately 5 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming.

G. Durability: Ships well.

PLANT

A. Foliage: Medium green with a zone.

*Form.*—Reniform, with cordate base.

*Margin.*—Crenate.

*Color.*—Adaxial: Green Group 137A with zone of Yellow-Green Group 147A. This can be compared to Green Group 137A with no zonation for the Precious cultivar. Abaxial: Green Group 137B. This can be compared to Green Group 137C for the Precious cultivar.

*Size.*—Approximately 7.0 to 7.5 cm. at the widest point and approximately 6.0 to 6.2 cm. at the narrowest point. This can be compared to approximately 6.0 to 6.3 cm. at the widest point and approximately 5.0 to 5.5 cm. at the narrowest point for the Precious cultivar.

*Tolerance to Botrytis.*—None claimed.

B. General appearance and form:

*Internode Length.*—Commonly varies from approximately 0.9 to 1.3 cm. compared to approximately 1.9 to 2.5 cm. for the Precious cultivar.

*Branching pattern.*—Freely basal branching. No pinching is required to obtain self-branching. A medium self-branching growth habit is exhibited in the absence of the use of a growth regulator.

*Height.*—Approximately 22 to 24 cm. above a 10 cm. pot a 9 weeks under standard greenhouse conditions. This can be compared to approximately 22 to 26 cm. for the Precious cultivar.

I claim:

1. A new and distinct cultivar of Geranium plant named Pink Pearl, substantially as herein shown and described, which:

(a) exhibits attractive perfectly formed semi-double light lavender pink florets with white eyes, (b) forms medium green foliage with zonation, and (c) exhibits a medium self-branching growth habit.

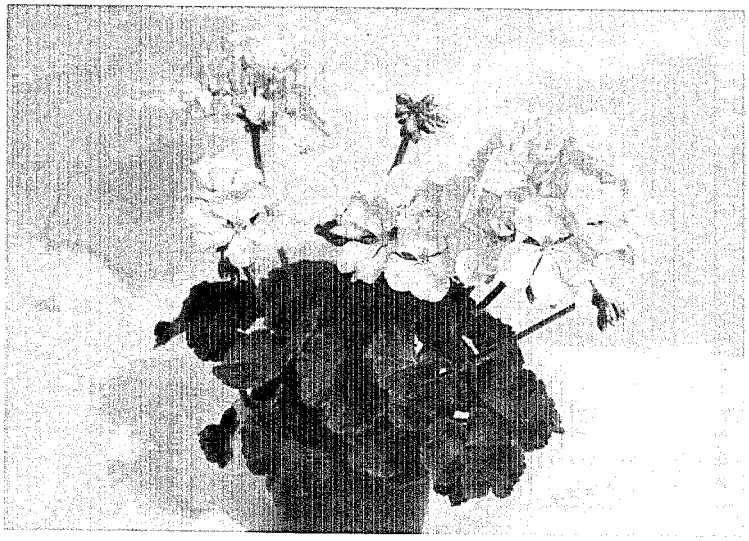

* * * * *